(12) United States Patent
Williams

(10) Patent No.: US 6,903,078 B1
(45) Date of Patent: Jun. 7, 2005

(54) COMBINATION PDGF, KGF, IGF, AND IGFBP FOR WOUND HEALING

(75) Inventor: Lewis T. Williams, Tiburon, CA (US)

(73) Assignee: Chiron Corporation, Emeryville, CA (US)

( * ) Notice: Subject to any disclaimer, the term of this patent is extended or adjusted under 35 U.S.C. 154(b) by 422 days.

(21) Appl. No.: 09/723,449

(22) Filed: Nov. 27, 2000

Related U.S. Application Data

(63) Continuation of application No. 08/719,742, filed on Sep. 25, 1996, now abandoned.
(60) Provisional application No. 60/021,540, filed on Jul. 11, 1996, and provisional application No. 60/005,075, filed on Oct. 11, 1995.

(51) Int. Cl.$^7$ ............................................... A61K 48/00
(52) U.S. Cl. ...................................... 514/44; 435/320.1
(58) Field of Search ........................ 514/44; 435/320.1; 536/23.1; 530/350; 424/198.1, 93.1, 93.2, 93.21

(56) References Cited

U.S. PATENT DOCUMENTS

| | | |
|---|---|---|
| 4,861,757 A | 8/1989 | Antoniades et al. |
| 5,019,559 A | 5/1991 | Antoniades et al. |
| 5,035,887 A | 7/1991 | Antoniades et al. |
| 5,187,263 A | 2/1993 | Murray |
| 5,399,361 A | 3/1995 | Song et al. |
| 5,407,913 A | 4/1995 | Sommer et al. |
| 5,422,120 A * | 6/1995 | Kim ........................... 424/450 |
| 5,624,893 A | 4/1997 | Yanni et al. |
| 5,677,278 A | 10/1997 | Gospodarowicz |
| 5,750,365 A * | 5/1998 | Chiu et al. .................. 435/69.1 |
| 5,773,586 A | 6/1998 | Gospodarowicz |
| 5,843,883 A | 12/1998 | Gospodarowicz |
| 5,863,767 A | 1/1999 | Gospodarowicz |
| 5,895,755 A * | 4/1999 | Murray ....................... 435/69.4 |
| 5,962,427 A * | 10/1999 | Goldstein et al. ............. 514/44 |

FOREIGN PATENT DOCUMENTS

| | | |
|---|---|---|
| WO | 123228 | 10/1984 |
| WO | 177957 | 4/1986 |
| WO | WO 88/03409 | 5/1988 |
| WO | 280460 | 8/1988 |
| WO | WO 90/08771 | 8/1990 |
| WO | 455422 | 11/1991 |
| WO | WO 92/03469 | 3/1992 |
| WO | WO 92/03470 | 3/1992 |
| WO | WO 92/03471 | 3/1992 |
| WO | WO 92/12243 | 7/1992 |
| WO | WO 92/14480 | 9/1992 |
| WO | WO 92/18154 | 10/1992 |
| WO | WO 93/04691 | 3/1993 |
| WO | 568334 | 11/1993 |
| WO | WO 94/04030 | 3/1994 |
| WO | WO 94/16723 | 8/1994 |
| WO | PCT/US96/15623 | 9/1996 |

OTHER PUBLICATIONS

Crystal, R.G. "Transfer of Genes to Humans: Early Lessons and Obstacles to Success" (1995) Science vol. 270, pp. 404–410.*

Verma, I. M. et al. "Gene Therapy– promises, Problems and Prospects" (1997) Nature vol. 389, pp. 239–242.*

Rozenberg, Y. et al., "Alternative Gene Delivery" (2001) S.T.P. Pharma Sci vol. 11, pp. 21–30.*

Nishikawa, M. et al. "Nonviral Vectors in The New Millennium: Delivery Barrier in Gene Transfer" (2001) Hum Gene Ther vol. 12, pp. 861–870.*

Balicki, D. et al. "Gene Therapy of Human Disease" (2002) Medicine vol. 81, pp. 69–86.*

Tseng, W. C. et al. "Liposome–Based Gene Therapy" (1998) Pharm Sci Technol vol. 1, No. 5, pp. 206–213.*

Lechardeur, D. et al. "Intracellular Barriers to Non–Viral Gene Transfer" (2002) Curr gene Ther vol. 2, No. 2, pp. 183–194.*

Jeschke, M.G. et al. "Possibilities of Non–Viral Gene transfer to Improve Cutaneous Wound Healing" (2001) Curr Gene Ther vol. 1 pp. 267–278.*

Fawcett, D. W. "A Textbook of Histology" Chapman & Hall, 1995, pp. 57–83.*

Jyung R.W. et al. Increased wound–breaking strength induced by insulin–like growth factor I in combination with insulin–like growth factor binding protein–1. Surgery, 1994; vol. 115(2), pp. 233–239.□ □.*

Marchese, C. et. al. Journal of Cellular Physiology 1990, vol. 144, No. 2, pges 326–332.*

Assouline et al., "Effect of Growth Factors on Collagen Lattice Contraction by Human Keratocytes," *Invest. Ophthalmology Visual Science* 33(5):1742–1755 (1992).

Danilenko et al., "Growth Factors in Porcine Full and Partial Thickness Burn Repair," *Am. J. Pathology* 147(5):1261–1277 (1995).

Doxey et al., "Platelet–Derived Growth Factor Levels in Wounds of Diabetic Rats," *Life Sciences* 57(11):1111–1123 (1995).

Jyung et al., "Increased Wound–Breaking Strength Induced by Insulin–Like Growth Factor I in Combination with Insulin–Like Growth Factor Binding Protein–1," *Surgery* 115(2):233–239 (1994).

(Continued)

Primary Examiner—Dave Trong Nguyen
Assistant Examiner—Jon Eric Angell
(74) Attorney, Agent, or Firm—Young J. Suh; Roberta L. Robins; Alisa A. Harbin

(57) ABSTRACT

The invention provides a therapeutic composition for epithelial wound repair that is a combination of PDGF and KGF. Further, the invention provides a composition for epithelial wound repair that is a therapeutic combination of PDGF, KGF, and IGF. Additionally, the invention provides a therapeutic composition of PDGF, KGF, IGF and IGFBP for epithelial wound repair.

2 Claims, No Drawings

OTHER PUBLICATIONS

Kratz et al., "Insulin Like Growth Factor–1 and –2 and Their Role in the Re–Epithelialisation of Wounds; Interaction with Insulin Like Growth Factor Binding Protein Type 1, " *Scand. J. Plant. Reconstr. Hand Surgery* 28:107–112 (1994).

Lynch et al., "Effects of the Platelet–Derived Growth Factor/ Insulin–Like Growth Factor–I Combination of Bone Regeneration Around Titanium Dental Implants. Results of a Pilot Study in Beagle Dogs," *J. of Periodotol* 62(11):710–716 (1991).

Lynch et al., *PNAS 84*:7696–7700 (1987).

Martin et al., *Progress in Growth Factor Research 4*:25–44 (1992).

Ring et al., "Growth Factors in Porcine Full and Partial Thickness Burn Repair," *Wound Repair and Regeneration,* Fifth Annual Meeting of the Wound Healing Society, Minneapolis, MN Apr. 27–30, 1995.

Staiano–Coico et al., "Human Keratinocyte Growth Factor Effects in a Porcine Model of Epidermal Wound Healing," *J. Exp. Med. 178*(3):865–878 (1993).

Sotozono et al., "Keratinocyte Growth Factor Accelerates Corneal Epithelial Wound Healing in Vivo," *Invest. Ophthalmology and Visual Science 36*(8):1524–1529 (1995).

Tarnow et al., "Topical Zinc–Oxide Treatment Increasee Endogenous Gene Expression of Insulin–Like Growth Factor–1in Granulation Tissue From Porcine Wounds," *Scand. J. Plant. Reconstr.Hand Surgery 28*:255–259 (1994).

Tsuboi et al., "Co–Administration of Insulin–Like Growth Factor (IGF)–I and IGF–Binding Protein–1 Stimulates Wound Healing in Animal Models," *J. Inv. Derm. 2*:199–203 (1995).

Werner et al., "The Function of KGF in Morphogenesis of Epithelium and Reepithelialization of Wounds," *Science 266*(5186):819–822 (1994).

Werner et al., "Large Induction of Keratinocyte Growth Factor Expression in the Dermis During Wound Healing," *Proc. Natl. Acad. Sci. U.S.A. 89*(15):6896–6900 (1992).

Pierce et al., "Pharmacologic Enhancement of Wound Healing," Annual Review of Medicine, 46:467–481 (1995).

* cited by examiner

COMBINATION PDGF, KGF, IGF, AND IGFBP FOR WOUND HEALING

CROSS-REFERENCE TO RELATED APPLICATIONS

This application is a continuation of U.S. patent application Ser. No. 08/719,742, filed Sep. 25, 1996, now abandoned, from which application priority is claimed pursuant to 35 U.S.C. §120, and this application is related to Provisional Patent Applications Ser. Nos. 60/005,075, filed Oct. 11, 1995 and 60/021,540, filed Jul. 11, 1996, from which priority is claimed under 35 USC §119(e)(1), and which applications are incorporated herein by reference in their entireties.

FIELD OF THE INVENTION

This invention relates to the use of a polypeptide having the biological activity of a platelet derived growth factor (PDGF) and a polypeptide having the biological activity of keratinocyte growth factor (KGF) for treatment or prevention of epithelial cell damage. This invention also relates to the use of a polypeptide having the biological activity of an insulin like growth factor (IGF-1 or IGF-2) in combination with the PDGF/KGF combination of the invention; the PDGF/KGF/IGF combination is useful for treatment or prevention of epithelial cell damage, being an improvement over previous methods for treating epithelial cell damage. The invention further relates to the use of a polypeptide having the biological activity of an insulin like growth factor binding protein (IGFBP) in combination with an IGF and further in combination with the PDGF/KGF combination of the invention. This invention further relates to pharmaceutical compositions including PDGF/KGF combination, PDGF/KGF/IGF, and PDGF/KGF/IGF/IGFBP combination for treatment or prevention of epithelial cell damage. This invention also relates to use of DNA encoding PDGF, DNA encoding KGF, DNA encoding an IGF, and DNA encoding an IGFBP for such treatment and prevention, as a PDGF/KGF combination or as a PDGF/KGF/IGF combination, or as a PDGF/KGF/IGF/IGFBP combination. Moreover, the present invention relates to kits containing PDGF and KGF, kits containing PDGF, KGF, and IGF, and kits containing PDGF, KGF, IGF, and IGFBP, and/or kits containing DNA encoding the three such combinations.

BACKGROUND OF THE INVENTION

The patent application EP 0 619 370 discloses the use of KGF for wound healing purposes. PDGF may also be used for wound healing purposes as evidenced by its ability to stimulate mesenchymal derived cells, as disclosed in U.S. Pat. No. 5,187,263.

Insulin like growth factors, IGF and IGF-2, have been described and studied in the art. IGF is described in Rinderknecht, *J. Biol. Chem.* 253:2769 (1978), and has been found to act as a mitogen on a number of different cell types as described in EP 0 128 733. Like insulin, the IGFs stimulate phosphorylation on specific tyrosine residues within the cytoplasmic domain of the receptors to which the IGF binds, as described in WO 93/98826. IGF-II is described in Rinderknecht, *FEBS Letters*, (1978) 89:283.

Insulin-like growth factors are also known under the class name somatomedins, and have been identified in various animal species as polypeptides that act to stimulate growth of cells in a variety of tissues and cell types, particularly during development. Growth promoting effects of somatomedins include enhancement of cell multiplication and stimulation of cartilage proliferation, stimulation of transport of amino acids, stimulation of synthesis of RNA, DNA and protein, and stimulation of incorporation of sulfate into proteoglycan and of proline into collagen. Much mammalian postnatal growth is due to stimulation of cartilage growth by somatomedins and growth in utero may also be somatomedin-dependent.

Uses of IGF as a known stimulatory and growth promoting agent includes use for bone repair and replacement therapy, as described in EP 303 855; as a means to counteract certain harmful side effects of carcinostatic drugs, as described in JP 63-196524; and as a way to increase lactation and meat production in cattle and other farm animals, as described in U.S. Pat. No. 4,783,524.

IGF-I has also been found useful in the treatment of osteoporosis in mammals exhibiting decreased cortical bone mineral density and those exposed to drugs or environmental conditions that result in bone density reduction and potentially to an osteoporosis condition, as described in EP 560 723 and EP 436 469.

IGF-I has been administered with sodium pentosan polysulfate (PPS) to severely osteoarthritic canines with the effect of reducing the severity of the disease by lowering the levels of active neutral metalloproteinase in the cartilage. In the model of mildly osteoarthritic canines, therapeutic intervention with IGF-I and PPS together appeared to successfully maintain cartilage structure and biochemistry, while IGF alone was ineffective, as described in Rogachefsky, *Osteoarthritis and Cartilage*, (1993) 1:105–114.

IGF binding proteins have been studied extensively, and presently six IGFBPs are known (IGFBP 1-6). IGFBPs form complexes with IGF-I and IGF-II in plasma and are believed to function typically as binding proteins for protein hormones, that is regulating the availability, the activity, and extending the half-life of the protein hormone ligand that they transport. While IGFBP-3, a 150 kDa complex, is the most abundant IGFBP in plasma and is believed to function as a carrier and reservoir of IGF-I in plasma, IGFBP-1 is a small 25 kDa binding protein produced mainly in the liver and fibroblasts, and can distribute between the circulation and the tissues, thus potentially regulating the bioavailability of IGF in both compartments as described in Tsuboi et al, *J. of Inv. Derm.* 104: 199–203 (1995). IGF has been described as useful for wound healing in combination with IGFBP, as described in Tsuboi et al, *J. of Inv. Derm.* 104: 199–203 (1995), Kratz et al, *Scand J Plast Reconsir Hand Surg.* 28:107–112 (1994), and Jyung et al, *Surgery* 115: 233–239 (1994).

IGF expression has been associated with wound healing as described in Gartner et al, *J. Surg. Res.* 52: 389–394 (1992), and Steenfos and Jansson, *Eur. J. Surg.* 158: 327–331 (1992). Additionally, IGF has been described as useful when administered in combination with PDGF for wound healing as described in U.S. Pat. No. 4,861,757.

Therefore, it would be advantageous if an improved composition can be found that would have improved properties over administration of PDGF alone, over administration of KGF alone, over PDGF with IGF, and over IGF alone, and over IGF with IGFBP.

SUMMARY OF THE INVENTION

It is, thus, an object of the present invention to provide an improved composition for treatment or prevention of epithelial yell damage. It is further an object of the present invention to provide an improved method for such treatment or prevention.

In accordance one of the objects of the present invention, there is provided herein a pharmaceutical composition for treatment or prevention of epithelial cell damage, the composition containing a first polypeptide having the biological activity of a platelet derived growth factor (PDGF) and a second polypeptide having the biological activity of keratinocyte growth factor (KGF).

In accordance one of the objects of the present invention, there is provided herein a pharmaceutical composition for treatment or prevention of epithelial cell damage, the composition containing a first polypeptide having the biological activity of a platelet derived growth factor (PDGF), a second polypeptide having the biological activity of keratinocyte growth factor (KGF), and a third polypeptide having the biological activity of insulin-like growth factor-1 (IGF-1).

Also in accordance with another object of the invention there is provided kits for treatment and prevention of epithelial cell damage comprising the pharmaceutical compositions of the invention as described herein.

In accordance with a further object of the present invention, there is provided methods of treatment or prevention of epithelial cell damage by applying to such cells the pharmaceutical compositions as described above.

In accordance with another object of the present invention, there is provided pharmaceutical compositions for treatment or prevention of epithelial cell damage by applying to such cells a pharmaceutical composition comprising a first DNA molecule including a first nucleotide sequence and a second DNA molecule including a second nucleotide sequence so that the first nucleotide sequence encodes PDGF and the second nucleotide sequence encodes KGF.

In accordance with another object of the present invention, there is provided pharmaceutical compositions for treatment or prevention of epithelial cell damage by applying to such cells a pharmaceutical composition comprising a first DNA molecule including a first nucleotide sequence, a second DNA molecule including a second nucleotide sequence, and a third DNA molecule including a third nucleotide sequence, so that the first nucleotide sequence encodes PDGF, the-second nucleotide sequence encodes KGF, and the third nucleotide sequence encodes IGF.

The pharmaceutical composition may also include a fourth polynucleotide having the biological activity of insulin-like growth factor binding protein (IGFBP).

Another embodiment of the invention is a method of repairing epithelial tissues comprising applying to the tissue to be repaired a pharmaceutical composition including KGF, PDGF, and alternatively IGF or IGF and IGFBP.

Yet another object of the invention is met with a method of repairing or preventing epithelial cell damage including applying to the cells to be protected or repaired the pharmaceutical composition that includes KGF and PDGF and further includes a composition with IGF.

Another object of the invention is a accomplished by a method of repairing or preventing epithelial cell damage including applying to the cells to be protected or repaired a pharmaceutical composition that includes KGF, PDGF and IGF, and that further includes a composition comprising an IGFBP.

A further object of the invention is met by a method of repairing epithelial cell damage comprising applying to the epithelial cell a pharmaceutical composition comprising a first DNA molecule, a second DNA molecule, and a third DNA molecule wherein the first DNA molecule is a first nucleotide sequence encoding PDGF, the second DNA molecule is a second nucleotide sequence encoding KGF, and the third DNA molecule is a third nucleotide sequence encoding IGF.

Yet a further object of the invention is met by a method of repairing epithelial cell damage comprising applying to the epithelial cell a pharmaceutical composition comprising a first DNA molecule, a second DNA molecule, a third DNA molecule, and a fourth DNA molecule wherein the first DNA molecule is a first nucleotide sequence encoding PDGF, the second DNA molecule is a second nucleotide sequence encoding KGF, the third DNA molecule is a third nucleotide sequence encoding IGF, and the fourth DNA molecule comprises a fourth nucleotide sequence encoding an IGFBP.

Another object of the invention is accomplished by a kit that has a first DNA molecule, a second DNA molecule and a third DNA molecule wherein the first DNA molecule is a first nucleotide sequence encoding PDGF, the second DNA molecule is a second nucleotide sequence encoding KGF, and the third DNA molecule is a third nucleotide sequence encoding IGF.

A final object of the invention is met by a kit that has a first DNA molecule, a second DNA molecule, a third DNA molecule, and a fourth DNA molecule wherein the first DNA molecule is a first nucleotide sequence encoding PDGF, the second DNA molecule is a second nucleotide sequence encoding KGF, the third DNA molecule is a third nucleotide sequence encoding IGF, and the fourth DNA molecule is a fourth nucleotide sequence encoding an IGFBP.

DETAILED DESCRIPTION OF THE PREFERRED EMBODIMENTS

This disclosure herein draws on previously published works such as scientific articles, published patents or patent applications. All such published works are incorporated herein by reference. The present invention can be better understood in light of the following definitions.

Definitions

Unless otherwise expressly provided herein, the term "platelet derived growth factor" or "PDGF" includes the PDGF A chain polypeptide and the PDGF B chain polypeptide and to the AA, BB, and AB dimers, and biologically active fragments, analogs, and derivatives thereof as described in U.S. Pat. No. 5,187,263; Waterfield et al., *Nature* 304:35–39 (1983); Wang et al., *J. Biol. Chem.* 259: 10645–48(1984), Antoniades et al., *Biochem. Pharm.* 33: 2833–38(1984); and Westermark et al., *Proc. Natl. Acad. Sci. USA* 83:7197–7200(1986); U.S. Pat. No. 5,219,759.

Also unless otherwise expressly provided herein, the term "keratinocyte growth factor" or "KGF" refers to any one of a mature polypeptide and biologically active fragments, analogs, and derivatives thereof as described in WO 90/08771 and WO 95/01434.

The term "insulin-like growth factor" as used herein encompasses IGF-I and IGF-II in their substantially purified, native, recombinantly produced, or chemically synthesized forms, and includes biologically active fragments, analogues, muteins, including C-terminal deletion muteins, and derivatives thereof that retain IGF activity and/or ability to bind the IGF receptors, as described in, for example, EP 135 094, WO 85/00831, U.S. Pat. No. 4,738,921, WO 92/04363, U.S. Pat. No. 5,158,875, EP 123 228, and EP 128 733. An analog of IGF or an analog of the fragment includes native IGF that has been modified by one or more amino acid insertion, deletion, or substitution that does not substantially affect its properties. Preferably, the analog has increased activity compared to native IGF. More preferably, at least 2-fold increase, most preferably, at least 7–10 fold increase. For example, the analog can include conservative amino acid substitutions. An IGF analog also includes peptides having one or more peptide mimics ("peptoids"), such as those described in WO 91/04282. An IGF mutein is polypeptide variant with one or more amino acids altered to produce a desired characteristic, such as to replace a cysteine residue with a non-disulfide bond forming amino acid. Muteins, analogues and derivatives may be generated using conventional techniques. For example, PCR mutagenesis can be used. While the following discussion refers to DNA, it is understood that the technique also finds application with RNA. An example of a PCR technique is described in WO 92/22653. Another method for making analogs, muteins, and derivatives, is cassette mutagenesis based on the technique described by Wells, *Gene*, (1985) 34:315.

The term "insulin like growth factor binding protein (IGFBP)" refers to a binding protein identified to bind an IGF binding protein as described and identified in Keifer et al, J. Biol. Chem. 266: 9043–9 (1991), Camacho-Hubner et al, *J. Biol. Chem.* 267: 11949–56 (1992), McCusker and Clemens, THE INSULIN LIKE GROWTH FACTORS: STRUCTURE AND BIOLOGICAL FUNCTIONS, Oxford Univ. Press, N.Y. pp. 110–150 (1992).

A polypeptide "having the biological activity of PDGF" refers to a polypeptide having the same or increased capability of preferentially stimulating the growth of cells of the dermis layer of the skin. Such a polypeptide can be a full-length PDGF, a fragment of PDGF, an analog of PDGF bearing amino acid substitution, deletion or addition or a derivative of PDGF, such as that described in U.S. Pat. No. 5,149,792 and EP 458 959 B1; and U.S. Pat. Nos. 4,769,328; 4,801,542; 4,766,073; 4,849,407; 4,845,075; 4,889,919; 5,045,633; and 5,128,321.

A polypeptide "having the biological activity of KGF" refers to a polypeptide having the same or increased capability of preferentially stimulating the growth of cells of the epidermis layer of the skin. Such a polypeptide can be a full-length KGF, a fragment of KGF, an analog of KGF bearing an amino acid substitution, deletion, or addition; or a derivative of KGF as described in WO 90/08771, and WO 95/01434.

A polypeptide "having the biological activity of IGF" refers to a polypeptide having the same or increased capability of acting as growth factor capable of insulin-like effects such as, for example, stimulation of phosphorylation of specific tyrosine residues within the cytoplasmic domain of the receptor to which it binds as described in WO 93/98826, or, in some cases, for example, mitogenic effects on certain cells as described in EP 0 128 733. Such a polypeptide can be full-length IGF, a fragment of IGF, an analog of IGF bearing an amino acid substitution, deletion, or addition, or any derivative of IGF.

A polypeptide "having the biological activity of IGFBP" refers to a polypeptide having about the same or an increased capability of acting as an IGF binding protein by binding and transporting IGF to tissue and cells where IGF-can have a biological effect. As there are presently at least six IGFBPs known, many of which significantly different from the other IGFBPs, specific qualities regarding the biological activity of a given IGFBP does not include necessarily the entire group of IGF binding proteins. Thus, the biological activity of an IGFBP may have some similarities to other IGFBPs, but may also have distinctions that identify it as a unique IGFBP.

"Full-length PDGF" or "mature PDGF" and "full-length KGF" or "mature KGF" and "full-length IGF" or "mature IGF", and "full length IGFBP" and "mature IGFBP" refers to the respective native polypeptide as found in human or other mammalian tissues.

The terms "analog" herein in reference to .PDGF, KGF, IGF, and IGFBP protein refers to truncations, variants, alleles and derivatives thereof. Unless specifically mentioned otherwise, these terms encompass the bioactivities of "mature" KGF or "mature" PDGF "mature" IGF or "mature" IGFBP. Thus, polypeptides that are identical or contain at least 60%, preferably 70%, more preferably 80%, and most preferably 90% sequence identity to the mature protein wherever derived, from human or nonhuman sources are included within this definition. The analogs herein further include peptides having one or more peptide mimics, also known as peptoids, that possess the bioactivity of the protein. Included within the definition are also polypeptides containing one or more analog amino acid (including, for example, unnatural amino acids, etc.), polypeptides with substituted linkages, as well as other modifications known in the art, both naturally occurring and nonnaturally occurring. The term polypeptide also does not exclude post-expression modifications of the polypeptide, for example, glycosylations, acetylations, phosphorylations and the like.

The "variants" and "derivatives" herein contain amino acid substitutions, deletions, or insertions. The amino acid substitutions can be conservative amino acid substitutions or substitutions to eliminate non-essential amino acid residues such as to alter a glycosylation site, a phosphorylation site, an acetylation site, or to minimize misfolding by substitution or deletion of one or more cysteine residues that are not necessary for function. Conservative amino acid substitutions are those that preserve the general charge, hydrophobicity/hydrophilicity and/or steric bulk of the amino acid substituted, for example, substitutions between the members of the following groups are conservative substitutions: Gly/Ala, Val/Ile/Leu, Asp/Glu, Lys/Arg, Asn/Gln, Ser/Cys/Thr and Phe/Trp/Tyr.

The term "polynucleotide" as used herein refers to a DNA molecule, a RNA molecule or its complementary strand thereof. A polynucleotide molecule can be single or double stranded.

A "therapeutically effective amount" as used herein refers to that amount of a composition that is effective to attain a desired result which, in the present instance, is repair of epithelial tissues. That amount can be in a single dose or as part of a series of doses. The precise amount will vary from subject to subject, depending on the subject's age, size, weight, and health, the nature and severity of the condition to be treated. It is not possible to specify an exact amount that is therapeutically effective in advance. However, the effective amount for a given situation can be determined by routine experimentation or based upon the experience of the person administering the composition based on the information provided herein. It is expected that the dose may fall within a relatively broad range.

"A pharmaceutically acceptable carrier" herein refers to any carrier that does not itself induce the production of antibodies harmful to the individual receiving the composition. Suitable carriers are typically large, slowly metabolized macromolecules such as proteins, polysaccharides, polylactic acids, polyglycolic acids, polymeric amino acids, amino acid copolymers and an inactive virus particle. Such carriers are well known to those of ordinary skill in the art. A thorough discussion of pharmaceutically acceptable excipients can be found in REMINGTON'S PHARMACEUTICAL- SCIENCES (Merck Pub. Co., N.J. 1991). Exemplary pharmaceutically acceptable carriers can include salts, for example, mineral acid salts such as hydrochlorides, hydrobromides, phosphates, sulfates, and the like; and the salts of organic acids such as acetates, propionates, malonates, benzoates, and the like.

The "pharmaceutical compositions" herein may further contain one or more components such as water, saline, glycerol, or ethanol. Additionally, auxiliary substances, such as wetting or emulsifying agents, pH buffering substances, stabilizers, antioxidants and the like may be present in such compositions. The pharmaceutical compositions herein may be prepared as a cream to be applied topically, or as liquid solutions or suspensions, or solid forms suitable for solution or suspension in liquid vehicles for injection. The pharmaceutical composition herein may be prepared in liposomal format such as those encapsulated in liposomes or in Depo-Foam$^R$; as described in U.S. Pat. No. 5,442,120; WO 95/13796; and WO 91/14445.

"Co-administration" as used herein means administration of KGF and PDGF according to the method of the invention in combination with each other, co-administration of KGF/PDGF and an IGF, and co-administration of KGF/PDGF/IGF/IGFBP. Co-administration also means administration of a PDGF/KGF combination also in combination with IGF or PDGF/KGF/IGF combination also in combination with IGFBP. Co-administration may be simultaneous, for example, by administering a mixture of KGF and PDGF, or a mixture of PDGF, KGF, and IGF, or IGF and IGFBP, or may be accomplished by administration of the agents separately, such as within a short time period. Co-administration also includes successive administration of KGF and PDGF, or successive administration of KGF, PDGF, and IGF, or successive administration of KGF, PDGF, and co-administration of IGF and IGFBP. Also, in the case of all these administrations, for example in the case of administration of KGF and PDGF, one of the two may be administered preventively while the other is administered thereafter for treatment, within a reasonable period of time after the preventive administration. For example, in the case of administration of KGF, PDGF, and IGF, or IGF and IGFBP, one or two or three may be administered preventively, and one or two or three may be administered thereafter for treatment, within a reasonable period of time after the preventive administration. Dosage treatment for administration or co-administration may be a single dose schedule or a multiple dose schedule.

The term "kit" refers to a package containing the specified material and includes printed instructions for use of the material. For example, a kit for the method of the invention may include PDGF and KGF polypeptides separately or in admixture or DNA encoding PDGF and KGF separately or in admixture, or as a combination of DNA and polypeptides, for example, the DNA of PDGF and the polypeptide of KGF. Also for example, a kit for the method of the invention may include PDGF, KGF, and IGF polypeptides separately or in admixture or DNA encoding PDGF, KGF and IGF separately or in admixture, or in a combination of DNA and polypeptides, for example, the DNA of PDGF and KGF, but the polypeptide of IGF. Also for example, a kit for the method of the invention may include PDGF, KGF, and IGF and IGFBP polypeptides separately or in admixture or DNA encoding PDGF, KGF and IGF IGFBP separately or in admixture, or in a combination of DNA and polypeptides, for example, the DNA of PDGF and KGF, but the polypeptide of IGF and the polypeptide IGFBP. "Printed instructions" may be written or printed on paper or other media, or committed to electronic media such as magnetic tape, computer-readable disks or tape, CD-ROM, and the like. Kits may also include plates, tubes, dishes, diluents, solvents, wash fluid or other conventional reagents.

The inventor has discovered, as disclosed herein, that the combination of PDGF and KGF or biologically active fragments, analogs or derivatives thereof, is more effective in treatment or prevention of epithelial cell damage than either PDGF or KGF alone. In addition, the inventor herein has discovered that the addition of IGF to the PDGF/KGF combination further improves the treatment or prevention of epithelial cell damage greatly beyond what might be expected by any of the three medicaments alone; and further in addition, the inventor herein has discovered that the addition of IGF and IGFBP to the PDGF/KGF combination further improves the treatment or prevention of epithelial cell damage greatly beyond what might be expected by any of the four medicaments alone, and even in addition to the improvements to epithelial cell damage derived by the administration of the PDGF/KGF combination, or the IGF/IGFBP combination.

In one embodiment of the present invention, a pharmaceutical composition contains a therapeutically effective amount of PDGF and KGF. Each of the PDGF and KGF can be made by any conventional techniques or can be purified from its natural sources. In a preferred embodiment of the present invention, each of PDGF and KGF is made by expression of a polynucleotide sequence encoding the respective protein in separate hosts or by coexpression thereof in a single host. The host cell can be prokaryotic or eukaryotic. For example PDGF can be made as described in U.S. Pat. No. 5,219,759. KGF can be made as described in WO 95/01434. Other expression systems can be used as described in greater detail below.

The pharmaceutical composition, in one embodiment of the present invention, can be either a composition containing PDGF alone and KGF alone, or both PDGF and KGF mixed together in a single composition, in either a single dose or multiple doses. In another embodiment of the present invention, for gene therapy purposes, the pharmaceutical composition can be a composition containing a polynucleotide encoding PDGF alone, a composition containing polynucleotide encoding KGF alone, or both polynucleotides mixed together in a single composition.

The PDGF and KGF compositions, if separately maintained, can be administered separately or contemporaneously. Direct delivery of the compositions will generally be accomplished by injection, either subcutaneously, intradermally, intraperitoneally, intraluminally, intragastrically, intraintestinally, intravenously or intramuscularly. Other modes of administration include oral and pulmonary administration, suppositories, and transdermal applications. Dosage treatment may be a single dose schedule or a multiple dose schedule.

In another embodiment of the present invention, a pharmaceutical composition contains a therapeutically effective amount of PDGF, KGF, and IGF. Each of the PDGF, KGF, and IGF can be made by any conventional techniques or can be purified from its natural sources. In a preferred embodiment of the present invention, each of PDGF, KGF, and IGF is made by expression of a polynucleotide sequence encoding the respective protein in separate hosts or by coexpression thereof in a single host. The host cell can be prokaryotic or eukaryotic. IGF can be made as described in U.S. Pat. No. 4,738,921. IGF can also be synthesized by the solid phase method as described in Li, *PNAS*, (1983) 80:2216–2220. In this method, the polypeptide sequence for IGF-I can be assembled by coupling the amino acid residues.

The PDGF, KGF and IGF compositions, if separately maintained, can be administered separately or contemporaneously. Direct delivery of the compositions will generally be accomplished by injection, either subcutaneously, intradermally, intraperitoneally, intraluminally, intragastrically, intraintestinally, intravenously or intramuscularly. Other modes of administration include oral and pulmonary administration, suppositories, and transdermal applications. Dosage treatment may be a single dose schedule or a multiple dose schedule.

In yet another embodiment, a pharmaceutical composition contains a therapeutically effective amount of PDGF, KGF, and IGF with IGFBP. Each of the PDGF, KGF, and IGF and IGFBP can be made by any conventional techniques or can be purified from its natural sources. In a preferred embodiment of the present invention, each of PDGF, KGF, and IGF and IGFBP is made by expression of a polynucleotide sequence encoding the respective protein in separate hosts or by coexpression thereof in a single host. The host cell can be prokaryotic or eukaryotic.

The PDGF, KGF, IGF, and IGFBP compositions, if separately maintained, can be administered separately or contemporaneously. Direct delivery of the compositions will generally be accomplished by injection, either subcutaneously, intradermally, intraperitoneally, intraluminally, intragastrically, intraintestinally, intravenously or intramuscularly. Other modes of administration include oral and pulmonary administration, suppositories, and transdermal applications. Dosage treatment may be a single dose schedule or a multiple dose schedule.

IGF can be made by conventional recombinant DNA techniques, as described in *Biochem. and Biophys. Res. Comm.*, (1990) 169:832–839 (IGF II) and *Cell Regulation*, (1990) 1:197–213, (IGF II), and *Biotechnology News*, (1983) 3:1–3 (IGF-I and II). For example, IGF can be produced in *E. coli* as a fusion protein with the trpE gene under the control of a modified tryptophan operon, as described in U.S. Pat. No. 4,738,921. Alternatively, IGF can be synthesized in *E. coli* under the control of the Vesicular Stomatitis Virus (VSV) promoter and protector sequences, as described in EP 478 333. The *E. coli* expression systems used for expression herein can be modified as described in U.S. Pat. No. 5,158,875, to include a modified positively charged leader sequence to enable. proper folding of the IGF protein. Moreover, IGF can be produced in methylotrophic yeast transformants with the IGF coding sequence linked to a signal sequence which direct secretion and proteolytic processing of the protein product. The signal sequence suitable herein includes the *S. cerevisiae* alpha mating factor pre-pro sequence in protease deficient *P. pastoris* strains, as described in WO 92/04363. DNA constructs for production of IGF-II can be made and expressed in *E. coli* as described in WO 89/03423. Synthesis of recombinant IGF-II can also be achieved by following the protocol described in EP 434 605, which relates to the production of recombinant IGF-II with a covalently attached foreign moiety and lacking the N-terminal attached methionine. IGF can also be made in yeast as described in EP 123 228 and U.S. patent application Ser. No. 06/922,199. Another method of producing IGF using recombinant DNA techniques that is suitable herein is as described in *Biotechnology News*, (1983) 10:1–3. IGF-I or IGF-II coding sequences can be inserted into viral or circular plasmid DNA vectors to form hybrid vectors, and the resulting hybrid vectors can be used to transform host microorganisms such as bacteria or yeast cells. The transformed microorganisms can be grown under appropriate nutrient conditions to express IGF, as described in EP 135 094. IGF can also be made as described in EP 434 625.

An IGFBP can be any known IGFBP, for example, IGFBP-1, IGFBP-2, IGFBP-3, IGFBP-4, IGFBP-5, and IGFBP-6. IGFBP can be made as described in Brinkman et al. *EMBO J.* 7: 2417–2423 (1988), Mohan et al, *Proc. Natl. Acad Sci USA* 86: 8338–42 (1989), U.S. Pat. No. 5,407,913, WO 92/12243, 92/03471, 92/03470, WO 92/03469, and Brewer et al, Biochem. Biophys. Res. Commun. 152: 1289–97(1988).

The pharmaceutical composition, in one embodiment of the present invention, can be either a composition containing PDGF alone, KGF alone, IGF alone, and IGF with IGFBP, or any two of the four mixed together, and the third and fourth alone, or any three of the four mixed together, and the fourth alone, or all four mixed together in a single composition, in either a single dose or multiple doses. In another embodiment of the present invention, for gene therapy purposes, the pharmaceutical composition can be a composition containing a polynucleotide encoding PDGF alone, a composition containing polynucleotide encoding KGF alone, a composition containing polynucleotide encoding IGF alone, a composition containing IGF and IGFBP only, or all four polynucleotides mixed together in a single composition.

The PDGF, KGF, IGF, and IGF with IGFBP compositions, if separately maintained, can be administered separately or contemporaneously. Additionally, the concentrations of each may be different, depending on the potency of the factor, and the needs of the patient. Direct delivery of the compositions will generally be accomplished by injection, either subcutaneously, intradermally, intraperitoneally, intraluminally, intragastrically, intraintestinally, intravenously or intramuscularly. Other modes of administration include oral and pulmonary administration, suppositories, and transdermal applications. Dosage treatment may be a single dose schedule or a multiple dose schedule.

Where PDGF, KGF, IGF or IGFBP are administered as polypeptides, either together in a single composition, or in multiple compositions, the polypeptides can be expressed by any expression system appropriate for the polypeptide.

Exemplary expression systems are listed below for generating the polypeptides of PDGF, KGF, IGF, and IGFBP or for cloning the polynucleotides encoding the same for application in a gene therapy protocol.

Expression in Bacterial Cells

Bacterial expression systems can be used with the present constructs. Control elements for use in bacteria include promoters, optionally containing operator sequences, and ribosome binding sites. Useful promoters include sequences derived from sugar metabolizing enzymes, such as galactose, lactose (lac) and maltose. Additional examples include promoter sequences derived from biosynthetic enzymes such as tryptophan (trp), the β-lactamase (bla) promoter system, bacteriophage λPL, and T7. In addition, synthetic promoters can be used, such as the lac promoter. The β-lactamase and lactose promoter systems are described in Chang et al., *Nature* (1978) 275: 615, and Goeddel et al., *Nature* (1979) 281: 544; the alkaline phosphatase, tryptophan (trp) promoter system are described in Goeddel et al., *Nucleic Acids Res.* (1980) 8: 4057 and EP 36,776 and hybrid promoters such as the lac promoter is described in U.S. Pat. No. 4,551,433 and deBoer et al., *Proc. Natl. Acad. Sci. USA* (1983) 80: 21–25. However, other known bacterial promoters useful for expression of eukaryotic proteins are also suitable. A person skilled in the art would be able to operably ligate such promoters to the present PDGF and KGF coding sequences, for example, as described in Siebenlist et al., *Cell*

(1980) 20: 269, using linkers or adaptors to supply any required restriction sites. Promoters for use in bacterial systems also generally will contain a Shine-Dalgano (SD) sequence operably linked to the DNA encoding the target polypeptide. For prokaryotic host cells that do not recognize and process the native target polypeptide signal sequence, the signal sequence can be substituted by a prokaryotic signal sequence selected, for example, from the group of the alkaline phosphatase, penicillinase, Ipp, or heat stable enterotoxin II leaders. The origin of replication from the plasmid pBR322 is suitable for most Gram-negative bacteria.

The foregoing systems are particularly compatible with *Escherichia coli*. However, numerous other systems for use in bacterial hosts including Gram-negative or Gram-positive organisms such as *Bacillus* spp., *Streptococcus* spp., *Streptomyces* spp., *Pseudomonas* species such as *P. aeruginosa*, *Salmonella typhimurium*, or *Serratia marcescans*, among others. Methods for introducing exogenous DNA into these hosts typically include the use of $CaCl_2$ or other agents, such as divalent cations and DMSO. DNA can also be introduced into bacterial cells by electroporation, nuclear injection, or protoplast fusion as described generally in Sambrook et al. (1989), cited above. These examples are illustrative rather than limiting. Preferably, the host cell should secrete minimal amounts of proteolytic enzymes. Alternatively, in vitro methods of cloning, e.g., PCR or other nucleic acid polymerase reactions, are suitable.

Also useful for expression of PDGF for the invention are vectors described in EP 0 622 456-A1, herein incorporated by reference, that disclose DNA for selection and autonomous replication in bacterial cells.

Prokaryotic cells used to produce the target polypeptide of this invention are cultured in suitable media, as described generally in Sambrook et al., cited above.

Expression in Yeast Cells

Expression and transformation vectors, either extrachromosomal replicons or integrating vectors, have been developed for transformation into many yeasts. For example, expression vectors have been developed for, among others, the following yeasts: *Saccharomyces cerevisiae*, as described in Hinnen et al., *Proc. Natl. Acad. Sci. USA* (1978) 75: 1929; Ito et al., *J. Bacteriol.* (1983) 153: 163; *Candida albicans* as described in Kurtz et al., *Mol. Cell. Biol.* (1986) 6: 142; *Candida maltosa*, as described in Kunze et al., *J. Basic Microbiol.* (1985) 25: 141; *Hansenula polymorpha*, as described in Gleeson et al., *J. Gen. Microbiol.* (1986) 132: 3459 and Roggenkarmp et al., *Mol. Gen. Genet.* (1986) 202: 302); *Kluyveromyces fragilis*, as described in Das et al., *J. Bacteriol.* (1984) 158: 1165; *Kluyveromyces lactis*, as described in De Louvencourt et al., *J. Bacteriol.* (1983) 154: 737 and Van den Berg et al., Bio/Technology (1990) 8: 135; *Pichia guillerimondii*, as described in Kunze et al. *J. Basic Microbiol.* (1985) 25: 141; *Pichia pastoris*, as described in Cregg et al., *Mol. Cell. Biol.* (1985) 5: 3376 and U.S. Pat. Nos. 4,837,148 and 4,929,555; *Schizosaccharomyces pombe*, as described in Beach and Nurse, *Nature* (1981) 300: 706; and *Yarrowia lipolytica*, as described in Davidow et al., *Curr. Genet.* (1985) 10: 380 and Gaillardin et al, *Curr. Genet.* (1985) 10: 49, *Aspergillus* hosts such as *A. nidulans*, as described in Ballance et al., *Biochem. Biophys. Res. Commun.* (1983) 112: 284–289; Tilburn et al., *Gene* (1983) 26: 205–221 and Yelton et al., *Proc. Natl. Acad. Sci. USA* (1984) 81: 1470–1474, and *A. niger*, as described in Kelly and Hynes, *EMBO J.* (1985) 4: 475479; *Trichoderma reesia*, as described in EP 0 244 234, and filamentous fungi such as, e.g, *Neurospora, Penicillium, Tolypocladium*, as described in WO 91/00357.

Control sequences for yeast vectors are known and include promoters regions from genes such as alcohol dehydrogenase (ADH), as described in EP 284,044, enolase, glucokinase, glucose-6-phosphate isomerase, glyceraldehyde-3-phosphate-dehydrogenase (GAP or GAPDH), hexokinase, phosphofructokinase, 3-phosphoglycerate mutase, and pyruvate kinase (PyK), as described in EP 329,203. The yeast PHO5 gene, encoding acid phosphatase, also provides useful promoter sequences, as described in Myanohara et al., *Proc. Natl. Acad. Sci. USA* (1983) 80: 1. Other suitable promoter sequences for use with yeast hosts include the promoters for 3-phosphoglycerate kinase, as described in Hitzeman et al, *J. Biol. Chem.* (1980) 255: 2073, or other glycolytic enzymes, such as pyruvate decarboxylase, triosephosphate isomerase, and phosphoglucose isomerase, as described in Hess et al., *J. Adv. Enzyme Reg.* (1968) 7: 149 and Holland et al, *Biochemistry* (1978) 17: 4900. Inducible yeast promoters having the additional advantage of transcription controlled by growth conditions, include from the list above and others the promoter regions for alcohol dehydrogenase 2, isocytochrome C, acid phosphatase, degradative enzymes associated with nitrogen metabolism, metallothionein, glyceraldehyde-3-phosphate dehydrogenase, and enzymes responsible for maltose and galactose utilization. Suitable vectors and promoters for use in yeast expression are further described in Hitzeman, EP 073,657. Yeast enhancers also are advantageously used with yeast promoters. In addition, synthetic promoters which do not occur in nature also function as yeast promoters. For example, upstream activating sequences (UAS) of one yeast promoter may be joined with the transcription activation region of another yeast promoter, creating a synthetic hybrid promoter. Examples of such hybrid promoters include the ADH regulatory sequence linked to the GAP transcription activation region, as described in U.S. Pat. Nos. 4,876,197 and 4,880,734. Other examples of hybrid promoters include promoters which consist of the regulatory sequences of either the ADH2, GAL4, GAL10, or PHO5 genes, combined with the transcriptional activation region of a glycolytic enzyme gene such as GAP or PyK, as described in EP 164,556. Furthermore, a yeast promoter can include naturally occurring promoters of non-yeast origin that have the ability to bind yeast RNA polymerase and initiate transcription.

Other control elements which may be included in the yeast expression vectors are terminators, for example, from GAPDH and from the enolase gene, as described in Holland et al., *J. Biol. Chem.* (1981) 256: 1385, and leader sequences which encode signal sequences for secretion. DNA encoding suitable signal sequences can be derived from genes for secreted yeast proteins, such as the yeast invertase gene as described in EP 012,873 and JP 62,096,086 and the a-factor gene, as described in U.S. Pat. Nos. 4,588,684, 4,546,083 and 4,870,008; EP 324,274; and WO 89/02463. Alternatively, leaders of non-yeast origin, such as an interferon leader, also provide for secretion in yeast, as described in EP 060,057.

Methods of introducing exogenous DNA into yeast hosts are well known in the art, and typically include either the transformation of spheroplasts or of intact yeast cells treated with alkali cations. Transformations into yeast can be carried out according to the method described in Van Solingen et al., *J. Bact.* (1977) 130: 946 and Hsiao et al., *Proc. Natl. Acad. Sci. USA* (1979) 76: 3829. However, other methods for introducing DNA into cells such as by nuclear injection, electroporation, or protoplast fusion may also be used as described generally in Sambrook et al., cited above.

For yeast secretion the native target polypeptide signal sequence may be substituted by the yeast invertase, α-factor, or acid phosphatase leaders. The origin of replication from the 2µ plasmid origin is suitable for yeast. A suitable selection gene for use in yeast is the trp1 gene present in the yeast plasmid described in Kingsman et al., *Gene* (1979) 7: 141 or Tschemper et al., *Gene* (1980) 10: 157. The trp1 gene provides a selection marker for a mutant strain of yeast lacking the ability to grow in tryptophan. Similarly, Leu2-deficient yeast strains (ATCC 20,622 or 38,626) are complemented by known plasmids bearing the Leu2 Gene.

For intracellular production of the present polypeptides in yeast, a sequence encoding a yeast protein can be linked to a coding sequence of the PDGF or the KGF polypeptide to produce a fusion protein that can be cleaved intracellularly by the yeast cells upon expression. An example, of such a yeast leader sequence is the yeast ubiquitin gene.

Expression in Insect Cells

Baculovirus expression vectors (BEVs) are recombinant insect viruses in which the coding sequence for a foreign gene to be expressed is inserted behind a baculovirus promoter in place of a viral gene, e.g., polyhedrin, as described in Smith and Summers, U.S. Pat. No., 4,745,051.

An expression construct herein includes a DNA vector useful as an intermediate for the infection or transformation of an insect cell system, the vector generally containing DNA coding for a baculovirus transcriptional promoter, optionally but preferably, followed downstream by an insect signal DNA sequence capable of directing secretion of a desired protein, and a site for insertion of the foreign gene encoding the foreign protein, the signal DNA sequence and the foreign gene being placed under the transcriptional control of a baculovirus promoter, the foreign gene herein being the coding sequence of the PDGF or the KGF polypeptide.

The promoter for use herein can be a baculovirus transcriptional promoter region derived from any of the over 500 baculoviruses generally infecting insects, such as, for example, the Orders *Lepidoptera, Diptera, Orthoptera, Coleoptera* and *Hymenoptera* including, for example, but not limited to the viral DNAs of *Autographo californica* MNPV, *Bombyx mori* NPV, *rrichoplusia ni* MNPV, *Rachlplusia ou* MNPV or *Galleria mellonella* MNPV. Thus, the baculovirus transcriptional promoter can be, for example, a baculovirus immediate-early gene IEI or IEN promoter; an immediate-early gene in combination with a baculovirus delayed-early gene promoter region selected from the group consisting of a 39K and a HindIII fragment containing a delayed-early gene; or a baculovirus late gene promoter. The immediate-early or delayed-early promoters can be enhanced with transcriptional enhancer elements.

Particularly suitable for use herein is the strong polyhedrin promoter of the baculovirus, which directs a high level of expression of a DNA insert, as described in Friesen et al. (1986) "The Regulation of Baculovirus Gene Expression" in: THE MOLECULAR BIOLOGY OF BACULOVIRUSES (W. Doerfler, ed.); EP 127,839 and EP 155,476; and the promoter from the gene encoding the p 10 protein, as described in Vlak et al. *J. Gen. Virol.* (1988) 69: 765–776.

The plasmid for use herein usually also contains the polyhedrin polyadenylation signal, as described in Miller et al., *Ann. Rev. Microbiol.* (1988) 42: 177 and a procaryotic ampicillin-resistance (amp) gene and an origin of replication for selection and propagation in *E. coli*. DNA encoding suitable signal sequences can also be included and is generally derived from genes for secreted insect or baculovirus proteins, such as the baculovirus polyhedrin gene, as described in Carbonell et al., *Gene* (1988) 73: 409, as well as mammalian signal sequences such as those derived from genes encoding human a-interferon as described in Maeda et al., *Nature* (1985) 315: 592–594; human gastrin-releasing peptide, as described in Lebacq-Verheyden et al., *Mol. Cell. Biol.* (1988) 8: 3129; human IL-2, as described in Smith et al., *Proc. Natl. Acad. Sci. USA* (1985) 82: 8404; mouse IL-3, as described in Miyajima et al., *Gene* (1987) 58: 273; and human glucocerebrosidase, as described in Martin et al., *DNA* (1988) 7:99.

Numerous baculoviral strains and variants and corresponding permissive insect host cells from hosts such as *Spodoptera frugiperda* (caterpillar), *Aedes aegypti* (mosquito), *Aedes albopictus* (mosquito), *Drosophila melanogaster* (fruitfly), and *Bombyx mori* host cells have been identified and can be used herein. See, for example, the description in Luckow et al., *Bio/Technology*(1988) 6: 47–55, Miller et al., in GENETIC ENGINEERING (Setlow, J. K. et al. eds.), Vol. 8 (Plenum Publishing, 1986), pp. 277–279, and Maeda et al., *Nature*, (1985) 315: 592–594. A variety of such viral strains are publicly available, e.g., the L-1 variant of *Autographa californica* NPV and the Bm-5 strain of *Bombyx mori* NPV. Such viruses may be used as the virus for transfection of host cells such as *Spodoptera frugiperda* cells.

Other baculovirus genes in addition to the polyhedrin promoter may be employed to advantage in a baculovirus expression system. These include immediate-early (alpha), delayed-early (beta), late (gamma), or very late (delta), according to the phase of the viral infection during which they are expressed. The expression of these genes occurs sequentially, probably as the result of a "cascade" mechanism of transcriptional regulation. Thus, the immediate-early genes are expressed immediately after infection, in the absence of other viral functions, and one or more of the resulting gene products induces transcription of the delayed-early genes. Some delayed-early gene products, in turn, induce transcription of late genes, and finally, the very late genes are expressed under the control of previously expressed gene products from one or more of the earlier classes. One relatively well defined component of this regulatory cascade is IEI, a preferred immediate-early gene of *Autographo californica* nuclear polyhedrosis virus (AcMNPV). IEI is pressed in the absence of other viral functions and encodes a product that stimulates the transcription of several genes of the delayed-early class, including the preferred 39K gene, as described in Guarino and Summers, *J. Virol.* (1986) 57: 563–571 and *J. Virol.* (1987) 61: 2091–2099 as well as late genes, as described in Guanno and Summers, *Virol.* (1988) 162: 444–451.

Immediate-early genes as described above can be used in combination with a baculovirus gene promoter region of the delayed-early category. Unlike the immediate-early genes, such delayed-early genes require the presence of other viral genes or gene products such as those of the immediate-early genes. The combination of immediate-arly genes can be made with any of several delayed-early gene promoter regions such as 39K or one of the delayed-early gene promoters found on the HindIII fragment of the baculovirus genome. In the present instance, the 39 K promoter region can be linked to the foreign gene to be expressed such that expression can be further controlled by the presence of IEI, as described in L. A. Guarino and Summers (1986a), cited above; Guarino & Summers (1986b) *J. Virol.*, (1986) 60: 215–223, and Guarino et al. (1986c), *J. Virol.* (1986) 60: 224–229.

Additionally, when a combination of immediate-early genes with a delayed-early gene promoter region is used, enhancement of the expression of heterologous genes can be realized by the presence of an enhancer sequence in direct cis linkage with the delayed-early gene promoter region. Such enhancer sequences are characterized by their enhancement of delayed-early gene expression in situations where the immediate-early gene or its product is limited. For example, the hr5 enhancer sequence can be linked directly, in cis, to the delayed-early gene promoter region, 39K, thereby enhancing the expression of the cloned heterologous DNA as described in Guarino and Summers (1986a), (1986b), and Guarino et al. (1986).

The polyhedrin gene is classified as a very late gene. Therefore, transcription from the polyhedrin promoter requires the previous expression of an unknown, but probably large number of other viral and cellular gene products. Because of this delayed expression of the polyhedrin promoter, state-of-the-art BEVs, such as the exemplary BEV system described by Smith and Summers in, for example, U.S. Pat. No. , 4,745,051 will express foreign genes only as a result of gene expression from the rest of the viral genome, and only after the viral infection is well underway. This represents a limitation to the use of existing BEVs. The ability of the host cell to process newly synthesized proteins decreases as the baculovirus infection progresses. Thus, gene expression from the polyhedrin promoter occurs at a time when the host cell's ability to process newly synthesized proteins is potentially diminished for certain proteins such as human tissue plasminogen activator. As a consequence, the expression of secretory glycoproteins in BEV systems is complicated due to incomplete secretion of the cloned gene product, thereby trapping the cloned gene product within the cell in an incompletely processed form.

While it has been recognized that an insect signal sequence can be used to express a foreign protein that can be cleaved to produce a mature protein, the present invention is preferably practiced with a mammalian signal sequence for example the PDGF or the KGF or the IGF or the IGFBP signal sequence.

An exemplary insect signal sequence suitable herein is the sequence encoding for a Lepidopteran adipokinetic hormone (AKH) peptide. The AKH family consists of short blocked neuropeptides that regulate energy substrate mobilization and metabolism in insects. In a preferred embodiment, a DNA sequence coding for a Lepidopteran *Manduca sexta* AKH signal peptide can be used. Other insect AKH signal peptides, such as those from the Orthoptera *Schistocerca gregaria* locus can also be employed to advantage. Another exemplary insect signal sequence is the sequence coding for *Drosophila* cuticle proteins such as CP1, CP2, CP3 or CP4.

Currently, the most commonly used transfer vector that can be used herein for introducing foreign genes into AcNPV is pAc373. Many other vectors, known to those of skill in the art, can also be used herein. Materials and methods for baculovirus/insect cell expression systems are commercially available in a kit form from companies such as Invitrogen (San Diego Calif.) ("MaxBac" kit). The techniques utilized herein are generally known to those skilled in the art and are fully described in Summers and Smith, A MANUAL OF METHODS FOR BACULOVIRUS VECTORS AND INSECT CELL CULTURE PROCEDURES, Texas Agricultural Experiment Station Bulletin No. 1555, Texas A&M University (1987); Smith et al., *Mol. Cell. Biol.* (1983) 3: 2156, and Luckow and Summers (1989). These include, for example, the use of pVL985 which alters the polyhedrin start codon from ATG to ATT, and which introduces a BamHI cloning site 32 basepairs downstream from the ATT, as described in Luckow and Summers, *Virology* (1989) 17:31.

Thus, for example, for insect cell expression of the present polypeptides, the desired DNA sequence can be inserted into the transfer vector, using known techniques. An insect cell host can be cotransformed with the transfer vector containing the inserted desired DNA together with the genomic DNA of wild type baculovirus, usually by cotransfection. The vector and viral genome are allowed to recombine resulting in a recombinant virus that can be easily identified and purified. The packaged recombinant virus can be used to infect insect host cells to express the PDGF and KGF polypeptides.

Other methods that are applicable herein are the standard methods of insect cell culture, cotransfection and preparation of plasmids are set forth in Summers and Smith (1987), cited above. This reference also pertains to the standard methods of cloning genes into AcMNPV transfer vectors, plasmid DNA isolation, transferring genes into the AcmMNPV genome, viral DNA purification, radiolabeling recombinant proteins and preparation of insect cell culture media. The procedure for the cultivation of viruses and cells are described in Volkman and Summers, *J. Virol.* (1975)19: 820–832 and Volkman, al., *J. Virol.* (1976)19: 820–832.

Expression in Mammalian Cells

Typical promoters for mammalian cell expression include the SV40 early promoter, the CMV promoter, the mouse mammary tumor virus LTR promoter, the adenovirus major late promoter (Ad MLP), and the herpes simplex virus promoter, among others. Other non-viral promoters, such as a promoter derived from the murine metallothionein gene, will also find use in mammalian constructs. Mammalian expression may be either constitutive or regulated (inducible), depending on the promoter. Typically, transcription termination and polyadenylation sequences will also be present, located 3' to the translation stop codon. Preferably, a sequence for optimization of initiation of translation, located 5' to the PDGF or the KGF polypeptide coding sequence, is also present. Examples of transcription terminator/polyadenylation signals include those derived from SV40, as described in Sambrook et al. (1989), cited previously. Introns, containing splice donor and acceptor sites, may also be designed into the constructs of the present invention.

Enhancer elements can also be used herein to increase expression levels of the mammalian constructs. Examples include the SV40 early gene enhancer, as described in Dijkema et al., EMBO J. (1985) 4: 761 and the enhancer/promoter derived from the long terminal repeat (LTR) of the Rous Sarcoma Virus, as described in Gorman et al., *Proc. Natl. Acad. Sci. USA* (1982b) 79: 6777 and human cytomegalovirus, as described in Boshart et al, *Cell* (1985) 41: 521. A leader sequence can also be present which includes a sequence encoding a signal peptide, to provide for the secretion of the foreign protein in mammalian cells. Preferably, there are processing sites encoded between the leader fragment and the gene of interest such that the leader sequence can be cleaved either in vivo or in vitro. The adenovirus tripartite leader is an example of a leader sequence that provides for secretion of a foreign protein in mammalian cells.

There exist expression vectors that provide for the transient expression in mammalian cells of DNA encoding the target polypeptide. In general, transient expression involves the use of an expression vector that is able to replicate efficiently in a host cell, such that the host cell accumulates many copies of the expression vector and, in turn, synthesizes high levels of a desired polypeptide encoded by the expression vector. Transient expression systems, comprising a suitable expression vector and a host cell, allow for the convenient positive identification of polypeptides encoded by cloned DNAs, as well as for the rapid screening of such polypeptides for desired biological or physiological properties. Thus, transient expression systems are particularly useful for purposes of identifying analogs and variants of the target polypeptide that have target polypeptide-like activity.

The expression vector as disclosed in EP 0622 456 A1 for expression of PDGF B chain is also useful for the invention for expression PDGF by a viral promoter functional in mammalian cells.

Once complete, the mammalian expression vectors can be used to transform any of several mammalian cells. Methods for introduction of heterologous polynucleotides into mammalian cells are known in the art and include dextran-mediated transfection, calcium phosphate precipitation, polybrene mediated transfection, protoplast fusion, electroporation, encapsulation of the polynucleotide(s) in liposomes, and direct microinjection of the DNA into nuclei. General aspects of mammalian cell host system transformations have been described by Axel in U.S. Pat. No. 4,399,216.

Mammalian cell lines available as hosts for expression are also known and include many immortalized cell lines available from the American Type Culture Collection (ATCC), including but not limited to, Chinese hamster ovary (CHO) cells, HeLa cells, baby hamster kidney (BHK) cells, monkey kidney cells (COS), human hepatocellular carcinoma cells (e.g., Hep G2), human embryonic kidney cells, baby hamster kidney cells, mouse sertoli cells, canine kidney cells, buffalo rat liver cells, human lung cells, human liver cells, mouse mammary tumor cells, as well as others.

The mammalian host cells used to produce the target polypeptide of this invention may be cultured in a variety of media. Commercially available media such as Ham's F10 (Sigma), Minimal Essential Medium ((MEM), Sigma), RPMI-1640 (Sigma), and Dulbecco's Modified Eagle's Medium ([DMEM], Sigma) are suitable for culturing the host cells. In addition, any of the media described in Ham and Wallace, *Meth. Enz.* (1979) 58: 44, Barnes and Sato, *Anal. Biochem.* (1980) 102: 255, U.S. Pat. No. 4,767,704, 4,657,866, 4,927,762, or 4,560,655, WO 90/103430, WO 87/00195, and U.S. RE 30,985, may be used as culture media for the host cells. Any of these media may be supplemented as necessary with hormones and/or other growth factors such as insulin, transferrin, or epidermal growth factor, salts (such as sodium chloride, calcium, magnesium, and phosphate), buffers (such as HEPES), nucleosides (such as adenosine and thymidine), antibiotics (such as Gentamycin(tm) M drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

Gene Therapy Administration of PDGF and KGF or PDGF, KGF and IGF or PDGF, KGF, IGF and IGFBP For gene therapy purposes, the polynucleotides encoding PDGF and KGF, or PDGF, KGF and IGF, or PDGF, KGF, IGF, and IGFBP can be administered to the animal for expression. Further, the polynucleotides can be administered either as naked polynucleotide, or can be linked with other polynucleotides for the purposes of delivery, such as viral vectors. Such polynucleotides can also be encapsulated in liposomes or other delivery means as conventional in the art. Examples of the uses of gene therapy protocols for administration of KGF, PDGF, IGF, and IGFBP are detailed below.

Where gene therapy techniques are applied to the invention, KGF and PDGF can be expressed by different vectors or by the same vector; also KGF, PDGF and IGF can be expressed by different vectors or by the same vector, also KGF, PDGF, IGF and IGFBP can be expressed by different vectors or by the same vector. The regulatory control of each gene product is distinct and a person skilled in the art of gene therapy and expression can select the appropriate regulatory sequences for both KGF and PDGF, or where IGF is also administered, regulatory sequences appropriate for KGF, PDGF and IGF, and where IGFBP is also administered, regulatory sequences also appropriate for IGFBP.

Alternatively, vectors comprising polynucleotide sequences encoding the KGF and PDGF polypeptides, and also IGF polypeptide where IGF is also administered, and also IGFBP where IGFBP is also administered, can be used directly for gene therapy and administered using standard gene delivery protocols. In this regard, the nucleotide sequences encoding the KGF and PDGF polypeptides, and also IGF where IGF is also administered, and IGFBP where IGFBP is also administered, can be stably integrated into the host cell genome or maintained on a stable episomal element in the host cell. Methods for gene delivery are known in the art, as described in U.S. Pat. No. 5,399,346.

Gene therapy strategies for delivery of constructs of the invention can utilize viral or non-viral vector approaches in in vivo or ex vivo modality. Expression of such coding sequence can be induced using endogenous mammalian or heterologous promoters. Expression of the coding sequence in vivo can be either constitutive or regulated.

For delivery using viral vectors, any of a number of viral vectors can be used, as described in Jolly, *Cancer Gene Therapy* 1: 51–64 (1994). For example, the coding sequence can be inserted into plasmids designed for expression in retroviral vectors, as described in Kimura el al., *Human Gene Therapy* (1994) 5: 845–852, adenoviral vectors, as described in Connelly et al., *Human Gene Therapy* (1995) 5: 185–193, adeno-associated viral vectors, as described in Kaplitt et al., *Nature Genetics* (1994) 6: 148–153 and sindbis vectors. Promoters that are suitable for use with these vectors include the Moloney retroviral LTR, CMV promoter and the mouse albumin promoter. Replication incompetent free virus can be produced and injected directly into the animal or humans or by transduction of an autologous cell ex vivo, followed by injection in vivo as described in Zatloukal et al., *Proc. Natl. Acad. Sci. USA* (1994) 91: 5148–5152.

The altered coding sequence can also be inserted into plasmid for expression of the polypeptide in vivo or ex vivo. For in vivo therapy, the coding sequence can be delivered by direct injection into tissue or by intravenous infusion. Promoters suitable for use in this manner include endogenous and heterologous promoters such as CMV. Further, a synthetic T7T7/T7OB promoter can be constructed in accordance with Chen et al. (1994), *Nucleic Acids Res.* 22: 2114–2120, where the T7 polymerase is under the regulatory control of its own promoter and drives the transcription of the coding sequence, which is also placed under the control of a T7 promoter. The coding sequence can be injected in a formulation comprising a buffer that can stablize the coding sequence and facilitate transduction thereof into cells and/or provide targeting, as described in Zhu et al., *Science* (1993) 261: 209–211.

Expression of the coding sequence in vivo upon delivery for gene therapy purposes by either viral or non-viral vectors can be regulated for maximal efficacy and safety by use of regulated gene expression promoters as described in Gossen et al., *Proc. Natl. Acad. Sci. USA* (1992) 89:5547–5551. For example, the coding sequence can be regulated by tetracycline responsive promoters. These promoters can be regulated in a positive or negative fashion by treatment with the regulator molecule.

For non-viral delivery of the coding sequence, the sequence can be inserted into conventional vectors that contain conventional control sequences for high level expression, and then be incubated with synthetic gene transfer molecules such as polymeric DNA-binding cations like polylysine, protamine, and albumin, linked to cell targeting ligands such as asialoorosomucoid, as described in Wu and Wu, *J. Biol. Chem.* (1987) 262: 4429–4432; insulin, as described in Hucked et al., *Biochem. Pharmacol.* 40: 253–263 (1990); galactose, as described in Plank et al., *Bioconjugate Chem.* 3:533–539 (1992); lactose, as described in Midoux et al., *Nucleic Acids Res.* 21: 871–878 (1993); or transferrin, as described in Wagner et al., *Proc. Natl. Acad. Sci. USA* 87:3410–3414 (1990). Other delivery systems include the use of liposomes to encapsulate DNA comprising the gene under the control of a variety of tissue-specific or ubiquitously-active promoters, as described in Nabel et al, *Proc. Natl. Acad. Sci. USA* 90: 11307–11311 (1993), and Philip et al., *Mol. Cell Biol.* 14: 2411–2418 (1994). Further non-viral delivery suitable for use includes mechanical delivery systems such as the biolistic approach, as described in Woffendin et al., *Proc. Natl. Acad. Sci. USA* (1994) 91(24): 11581–11585. Moreover, the coding sequence and the product of expression of such can be delivered through deposition of photopolymerized hydrogel materials. Other conventional methods for gene delivery that can be used for delivery of the coding sequence include, for example, use of hand held gene transfer particle gun, as described in U.S. Pat. No. 5,149,655; use of ionizing radiation for activating transferred gene, as described in U.S. Pat. No. 5,206,152 and PCT application WO 92/11033.

Application of gene therapy technology with regard to the peptides and polypeptides of the invention and their analogues or variants can be made where it is beneficial to treat a wound by gene therapy, for example, with chronic wounds such as ulcers, or with any wound in which the cells at the site of the wound are responsive to a gene therapy protocol.

In general, gene therapy can be applied according to the invention in all situations where it is beneficial to heal a wound by administering according to a gene therapy protocol, of a sufficient amount of a peptide of the invention or its analogue, variant, or dominant negative, for example, for modulating the normal activity of binding pair interactions. Subsequent administration may be required depending on the condition of the wound and the environment with which it is presented.

Vectors encoding the KGF, PDGF, IGF, and IGFBP polypeptides can also be packaged in liposomes prior to delivery to the subject or to cells derived therefrom. Lipid encapsulation is generally accomplished using liposomes which are able to stably bind or entrap and retain nucleic acid. The ratio of condensed DNA to lipid preparation can vary but will generally be around 1:1 (mg DNA:micromoles lipid), or more of lipid. For a review of the use of liposomes as carriers for delivery of nucleic acids, see, Hug and Sleight, *Biochim. Biophys. Acta.* 1097:1–17 (1991); Straubinger et al. *Methods of Enzymology*, 101: 512–527 (1983).

Liposomal preparations for use in the instant invention include cationic (positively charged), anionic (negatively charged) and neutral preparations, with cationic liposomes particularly preferred. Cationic liposomes have been shown to mediate intracellular delivery of plasmid DNA (Felgner et al. *Proc. Natl. Acad. Sci. USA* (1987) 84:7413–7416); mRNA (Malone et al. *Proc. Natl. Acad. Sci. USA* (1989) 86:6077–6081); and purified transcription factors (Debs et al. *J. Biol. Chem.* (1990) 265:10189–10192), in functional form.

Cationic liposomes are readily available. For example, N[1-2,3-dioleyloxy)propyl]-N,N,N-triethylammonium (DOTMA) liposomes are available under the trademark Lipofectin, from GIBCO BRL, Grand Island, N.Y. (See, also, Felgner et al. *Proc. Natl. Acad. Sci. USA* (1987) 84:7413–7416). Other commercially available liposomes include transfectace (DDAB/DOPE) and DOTAP/DOPE (Boerhinger). Other cationic liposomes can be prepared from readily available materials using techniques well known in the art. See, e.g., Szoka et al. *Proc. Natl. Acad. Sci. USA* (1978) 75:4194–4198; PCT Publication No. WO 90/11092 for a description of the synthesis of DOTAP (1,2-bis(oleoyloxy)-3-(trimethylammonio)propane) liposomes.

Similarly, anionic and neutral liposomes are readily available, such as from Avanti Polar Lipids (Birmingham, Ala.), or can be easily prepared using readily available materials. Such materials include phosphatidyl choline, cholesterol, phosphatidyl ethanolamine, dioleoylphosphatidyl choline (DOPC), dioleoylphosphatidyl glycerol (DOPG), dioleoylphoshatidyl ethanolamine (DOPE), among others. These materials can also be mixed with the DOTMA and DOTAP starting materials in appropriate ratios. Methods for making liposomes using these materials are well known in the art.

The liposomes can comprise multilammelar vesicles (MLVs), small unilamellar vesicles (SUVs), or large unilamellar vesicles (LUVs). The various liposome-nucleic acid complexes are prepared using methods known in the art. See, e.g., Straubinger et al. in *Methods of Immunology* (1983), Vol. 101, pp. 512–527; Szoka et al. *Proc. Natl. Acad Sci. USA* (1978) 75:4194–4198; Papahadjopoulos et al. *Biochim. Biophys. Acta* (1975) 394:483; Wilson et al. *Cell* (1979) 17:77); Deamer and Bangham *Biochem. Biophys. Acta* (1976) 443:629; Ostro et al. *Biochem. Biophys. Res. Commun.* (1977) 76:836; Fraley et al. *Proc. Natl. Acad. Sci. USA* (1979) 76:3348); Enoch and Strittmatter *Proc. Natl. Acad. Sci. USA* (1979) 76:145); Fraley et al. *J. Biol. Chem.* (1980) 255:10431; Szoka and Papahadjopoulos *Proc. Natl. Acad. Sci. USA* (1978) 75:145; and Schaefer-Ridder et al. *Science* (1982) 215:166.

Liposomes are included within the definition of a pharmaceutically acceptable carrier. The term "liposomes" refers to, for example, the liposome compositions described in U.S. Pat. No. 5,422,120, WO 95/13796, WO 94/23697, WO 91/14445 and EP 524,968 B1. Liposomes may be pharmaceutical carriers for the polynucleotides or polypeptides of the invention, or for combination of the two. The therapeutic agent may be conjugated to a liposome, or may be conjugated to a hydrogel polymer, and the hydrogel polymer (or a component of a hydrogel polymer) conjugated or encapsulated by a liposome.

The recombinant vectors (whether or not encapsulated in liposomes), may be administered in pharmaceutical compositions as described above. The pharmaceutical compositions will comprise sufficient genetic material to produce a therapeutically effective amount of the analog or analogs, as described above. For purposes of the present invention, an effective dose will be from about 0.05 mg/kg to about 50 mg/kg of the DNA constructs in the individual to which it is administered.

Once formulated, the compositions of the invention can be administered directly to the subject or, alternatively, in the case of the vectors described above, delivered ex vivo, to cells derived from the subject. Methods for the ex vivo delivery and reimplantation of transformed cells into a subject are known in the art and described in, for example, WO 93/14778. Generally, such methods will include dextran-mediated transfection, calcium phosphate precipitation, polybrene mediated transfection, protoplast fusion, electroporation, encapsulation of the polynucleotide(s) in liposomes, and direct microinjection of the DNA into nuclei, all well known in the art.

Administration of the therapeutic combinations of the invention can be accomplished by, for example, topical cream, foam, injection, aerosol spray, in a gel matrix, a sponge, drops, and a wash. Administration can be by, for example, local, oral, intradermal, subcutaneous, intraluminal, intragastric, and intraperitoneal administration with an appropriate formulation of the selected composition made up of a combination of the therapeutics appropriate for a particular treatment.

The therapeutics of the invention can be administered in a therapeutically effective dosage and amount, in the process of a therapeutically effective protocol for treatment of the patient. The initial and any subsequent dosages administered will depend upon the patient's age, weight, condition, and the disease, wound, disorder or biological condition being treated. Depending on the therapeutic, the dosage and protocol for administration will vary, and the dosage will also depend on the method of administration selected, for example, local or systemic administration.

The wound to which the therapeutic combinations are applied can be internal or external, and may be directed towards any tissue exhibiting a wound, for example epithelial tissue. For topical administration of IGF, a zinc oxide formulation can be applied, which induces the local production of IGF, as described in Tarnow et al, *Scand J. Plast Reconstr Hand Surg.* 28: 255–259 (1994). Administration of the therapeutic combinations of the invention can be accomplished with any combination of the therapeutics, for example, by administering PDGF and KGF followed by IGF with IGFBP, or by administering PDGF, KGF, IGF, and IGFBP at the same time or in close proximity in time. The dosages of each therapeutic for a given wound and a particular patient, are designed to achieve a maximum effective dose for the therapeutic. The dosages appropriate for a given treatment may depend on the particular combination of therapeutics selected for treatment. For example, IGF alone has been shown to be less potent than IGF administered in conjunction with IGFBP.

The doses for a particular wound will be determined on a patient by patient basis, and depend on the size of the wound, the type of injury, and the composition that is applied. Doses for the individual therapeutics have been determined within ranges. For example, an effective dose of PDGF has been determined to be 5 $ng/mm^2$ or higher when applied topically as described in U.S. Pat. No. 4,861,757, and at least 1 ng/ml local concentration of an isoform of PDGF (for example, PDGF-AA, PDGF-BB, or PDGF-AB)., up to about 30 ng/ml local concentration applied to a population of fibroblasts as described in Lepisto et al, *Biochem Biophys Res. Comm* 209: 393–399 (1995). PDGF can be administered in a carboxymethylcellulose gel formulation at concentrations of about 10 µg/gm to about 500 µg/gm of gel, about 20 µg/gm to about 200 µg/gm, and about 30 µg/gm to about 100 µg/gm of gel, optimally about 100 µg/gm of gel. Efficacy of PDGF has been achieved within the range of about 3 µg/ml solution to about 300 µg/ml of solution administered.

About 50 ul of KGF of a concentration of about 5 ug/ml is effective for wound healing by topical application to epithelial tissue as described in Sotozono et al, *Invest. Opthal. Vis. Science* 36: 1524–29 (1995). As described in U.S. Pat. No. 4,861,757, an effective amount of IGF when co-administered with PDGF is in the range of at least 2.5 $ng/mm^2$ to about 5 $ng/mm^2$, with a ratio of PDGF to IGF in the range of about 1:10 to about 25:1 weight to weight, with the most effective ratios being PDGF to IGF of about 1:1 to about 2:1 weight to weight. IGFBP administered in combination with IGF has been shown to increase wound healing at dose levels of about 5 ug of IGF with about 1.5 ug of phosphorylated IGFBP in a molar ration of about 11:1 IGF:IGFBP, as described in Jyung et al, *Surgery* 115:233–239 (1994).

For administration of polypeptide therapeutics, for example, a PDGF, KGF, IGF and IGFBP polypeptides, the dosage can be in the range of about 5 µg to about 50 µg/kg of tissue to which the application is directed, also about 50 µg to about 5 mg/kg, also about 100 µg to about 500 µg/kg of tissue, and about 200 to about 250 ug/kg. For polynucleotide therapeutics, for example in a gene therapy administration protocol, depending on the expression strength the polynucleotide in the patient, for tissue targeted administration, vectors containing expressible constructs including PDGF, KGF, IGF, and IGFBP coding sequences can be administered in a range of about 100 ng to about 200 mg of DNA for local administration in a gene therapy protocol, also about 500 ng to about 50 mg, also about 1 ug to about 2 mg of DNA, about 5 ug of DNA to about 500 ug of DNA, and about 20 ug to about 100 ug during a local administration in a gene therapy protocol, and about 250 ug, per injection or administration. Factors such as method of action and efficacy of transformation and expression are therefore considerations that will effect the dosage required for ultimate efficacy for administration of DNA therapeutics. Where greater expression is desired, over a larger area of tissue, larger amounts of DNA or the same amounts readministered in a successive protocol of administrations, or several administrations to different adjacent or close tissue portions of for example, a wound site may be required to effect a positive therapeutic outcome. In all cases, routine experimentation in clinical trials will determine specific ranges for optimal therapeutic effect, for each therapeutic, each administrative protocol, and administration to specific patients will also be adjusted to within effective and safe ranges depending on the patient condition and responsiveness to initial administrations.

Further objects, features, and advantages of the present invention will become apparent from the detailed description. It should be understood, however, that the detailed description, while indicating preferred embodiments of the invention, is given by way of illustration only, since various changes and modifications within the spirit and scope of the invention will become apparent to those skilled in the art from this detailed description. The following examples are exemplary only, and are not intended to limit the invention.

The present invention will now be illustrated by reference to the following examples which set forth particularly advantageous embodiments. However, it should be noted that these embodiments are illustrative and are not to be construed as restricting the invention in any way.

EXAMPLE 1

Second degree burns are treated with a spray formulation including 10 ug/ml of KGF, 30 ng/ml of a PDGF isoform, 10 ng/ml IGF-1, and 30 ng/ml of IGFBP-1. The spray is allowed to dry in the air. Re-application is suggested every couple of hours.

EXAMPLE 2

A suture wound is closed and a topical salve made up of 10% KGF and 5% PDGF is applied on the suture before bandaging. Re-application of the salve is directed 3 times daily.

EXAMPLE 3

A 20% zinc oxide formulation containing also 5% KGF, 2.5% PDGF, and 10% IGFBP is applied to minor abrasions, sunburns and chafing for faster healing of these wounds.

EXAMPLE 4

A liposomal formulation is used to encapsulate KGF, PDGF, IGF and IGFBP DNA each in a vector for expression. The ration of DNA by weight is 10:5:2.5:7.5, respectively. The liposomal composition is administered in a gel capsule by mouth for treatment of gastrointestinal ulcers with re-administration daily for a period of about a month, or until significant improvement dictates reduced frequency of administration.

What is claimed is:

1. A method of repairing epithelial cell damage comprising applying directly to the site of epithelial cell damage a pharmaceutical composition comprising a first DNA molecule, a second DNA molecule, a third DNA molecule, and a fourth DNA molecule wherein the first DNA molecule comprises a first nucleotide sequence encoding PDGF, the second DNA molecule comprises a second nucleotide sequence encoding KGF, wherein the second DNA molecule further comprises a secretion leader encoding nucleotide sequence, where the secretion leader is sufficient for secretion of KGF, the third DNA molecule comprises a third nucleotide sequence encoding IGF, and the fourth DNA molecule comprises a fourth nucleotide sequence encoding an IGFBP, wherein the first, second, third and fourth nucleotide sequences are operably linked to control elements that provide for expression thereof at the site of epithelial cell damage.

2. A kit comprising a first DNA molecule, a second DNA molecule, a third DNA molecule, and a fourth DNA molecule wherein the first DNA molecule comprises a first nucleotide sequence encoding PDGF, the second DNA molecule comprises a second nucleotide sequence encoding KGF, the third DNA molecule comprises a third nucleotide sequence encoding IGF, and the fourth DNA molecule comprises a fourth nucleotide sequence encoding an IGFBP.

* * * * *